(12) United States Patent
Chevalier et al.

(10) Patent No.: US 6,284,281 B1
(45) Date of Patent: Sep. 4, 2001

(54) COSMETIC COMPOSITION COMPRISING PARTICLES OF MELAMINE-FORMALDEHYDE OR UREA-FORMALDEHYDE RESIN AND ITS USES

(75) Inventors: Veronique Chevalier, Villercresness; Valerie Hurel, Gif/s/Yvette; Pascal Simon, Vitry sur Seine, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/542,458

(22) Filed: Apr. 4, 2000

(30) Foreign Application Priority Data

Apr. 21, 1999 (FR) .................................................. 99 05043

(51) Int. Cl.$^7$ ................................ A61K 9/14; A61K 7/00; A61K 31/74; A61K 7/42; A61K 47/00
(52) U.S. Cl. ............................ 424/489; 424/401; 424/59; 424/78.03; 514/937; 514/770; 514/772.3
(58) Field of Search ..................................... 424/401, 489, 424/78, 78.03, 59

(56) References Cited

U.S. PATENT DOCUMENTS

| | | |
|---|---|---|
| 5,219,561 | 6/1993 | Gagnebien et al. . |
| 5,939,079 | * 8/1999 | Le Royer et al. .................. 424/401 |

FOREIGN PATENT DOCUMENTS

| | | |
|---|---|---|
| 0 486 394 | 5/1992 | (EP) . |
| 0 651 991 | 5/1995 | (EP) . |

* cited by examiner

Primary Examiner—Thurman K. Page
Assistant Examiner—Blessing Fubara
(74) Attorney, Agent, or Firm—Oblon, Spivak, McClelland, Maier & Neustadt, P.C.

(57) ABSTRACT

Cosmetic composition comprising particles of melamine-formaldehyde or urea-formaldehyde resin and its uses. The present application relates to a composition comprising, in a physiologically acceptable medium, at least one oily phase and particles of melamine-formaldehyde or urea-formaldehyde resin, to the use of the said composition, especially as a cosmetic composition for caring for and/or making up the skin, in particular for softening defects of the relief of the skin, such as microrelief features, wrinkles or pores, while conferring a natural appearance on the skin, and to its use in treating greasy skin. The particles advantageously have a number-average size ranging from approximately 0.1 to 20 μm. The composition of the invention can be anhydrous or can be provided in the form of a water-in-oil or oil-in-water emulsion. The invention also relates to the use of particles of melamine-formaldehyde or urea-formaldehyde resin as mattifying agent in a cosmetic composition.

23 Claims, No Drawings

COSMETIC COMPOSITION COMPRISING PARTICLES OF MELAMINE-FORMALDEHYDE OR UREA-FORMALDEHYDE RESIN AND ITS USES

BACKGROUND OF THE INVENTION

1. Field of the Invention

The present application relates to a composition, in particular a cosmetic composition, comprising an oily phase and particles of melamine-formaldehyde or urea-formaldehyde resin, to its use as a composition for caring for and/or for making up the skin, in particular for softening defects of the relief of the skin, such as microrelief features, wrinkles or pores, while conferring a natural appearance on the skin, and to its use in treating greasy skin. The application also relates to the use of particles of melamine-formaldehyde or urea-formaldehyde resin as mattifying agent in a cosmetic composition.

2. Discussion of the Background

By definition, a mattifying product is a product which prevents the skin from shining and which gives a uniform complexion. Care compositions for the skin or make-up compositions having mattifying properties are generally used to solve the problems of shininess brought about by an excess of sebum and to improve the long term hold of make-up, which has a tendency to visually deteriorate during the course of the day. They give a matt appearance to the skin, resulting from a light scattering ability at the surface of the skin. They can also be used to soften skin defects, such as microrelief features, wrinkles, fine lines, pores or color variations.

Conventional so-called mattifying compositions generally comprise powders which adsorb sebum and the excess oil of the composition not adsorbed by the skin. Mention may in particular be made, among mattifying powders of natural or synthetic origin, of fillers, such as talc, starch, mica, silica, nylon powders, polyethylene powders, poly(β-alanine) or poly(methyl (meth)acrylate) powders. Fillers of this type exhibit the disadvantage of giving the skin an unnatural powdery appearance which can even accentuate skin defects. Furthermore, the compositions comprising them generally have a long term desiccating effect and are difficult to spread. Their mattifying effect is not very long lasting.

EP-A-0,502,769 discloses mattifying compositions which contribute a translucent layer and a natural appearance to made-up skin. They are dispersions of spherical particles in a fatty binder in a highly specific filler/binder ratio by weight. A high proportion of powders is necessary for a mattifying effect and, for this reason, these compositions can be desiccating. In addition, they have a tendency to become fluffy during spreading and to give a whitening effect to the skin because of the high concentration of powders.

The need therefore still remains for a mattifying composition which is comfortable during application and which does not result in any irritation or desiccation of the skin after application.

SUMMARY OF THE INVENTION

The Inventors have now found a composition which overcomes the disadvantages discussed above.

The Inventors have discovered, surprisingly, that the use of particles of melamine-formaldehyde or urea-formaldehyde resin in a composition comprising an oily phase confers, on this composition, a matt appearance on the skin, this matt appearance being obtained over a prolonged time and even with a fairly low proportion of particles. Furthermore, the composition obtained is comfortable for and does not dry out the skin.

Accordingly, the present invention provides a composition comprising, in a physiologically acceptable medium, at least one oily phase and particles of at least one resin chosen from melamine-formaldehyde resins and urea-formaldehyde resins.

The present invention also provides a method of cosmetically treating skin, comprising applying the inventive composition to the skin.

The present invention also provides a method of softening imperfections of the relief of the skin and/or for concealing microrelief features, wrinkles, fine lines and/or pores of the skin, comprising applying the inventive composition to the skin.

The present invention also provides a method of producing a matt appearance on skin, comprising applying the inventive composition to the skin.

The present invention also provides a method of concealing defects of the relief of the skin, comprising applying the inventive composition to the skin.

The present invention also provides a method of treating greasy skin, comprising applying the inventive composition to greasy skin.

The present invention also provides a method of preparing the inventive composition, comprising combining the oily phase, resin particles and physiologically acceptable medium.

As used herein, the term "physiologically acceptable medium" refers to a nontoxic medium capable of being applied to the skin (including the inside of the eyelids) or the lips of human beings.

The composition of the invention, by virtue of the presence of the resin particles, makes it possible to give a matt appearance to the skin. A further subject-matter of the invention is consequently the use of particles of at least one resin chosen from melamine-formaldehyde resins and urea-formaldehyde resins as mattifying agent in a cosmetic composition.

A more complete appreciation of the invention and many of the attendant advantages thereof will be readily obtained as the same becomes better understood by reference to the following detailed description.

DETAILED DESCRIPTION OF THE INVENTION

The melamine-formaldehyde resins and urea-formaldehyde resins used according to the invention are provided in the form of a powder, the particles of which have a number-average size ranging from approximately 0.1 to 20 μm, depending on the resin, inclusive of all specific values and subranges therebetween such as 0.2, 0.5, 1, 2, 5, 10, 15 and 18 μm. The particles of melamine-formaldehyde resin generally have a number-average size ranging from approximately 0.1 to 0.5 μm and they can form agglomerates ranging up to 5 μm. The particles of urea-formaldehyde resin generally have a number-average size ranging from approximately 5 to 20 μm.

Examples of particles of resin which can be used in the composition of the invention, of, for example, the melamine-formaldehyde resins sold under the name Microsilk MP by Grantee, under the name Fluidifiant FL01 by Lafarge or under the name Chrysogyplast PL 100-R by Chryso and the urea-formaldehyde resins sold under the names Pergopak, such as Pergopak M3, by Martinswerk.

The amount of particles of melamine-formaldehyde resin and/or of urea-formaldehyde resin in the composition of the invention may vary over a wide range. The amount can range, for example, from 0.05 to 20% and preferably from 0.1 to 10% by weight with respect to the total weight of the composition. These ranges include all specific values and subranges therebetween, such as 0.2, 0.5, 1, 2, 5, 8, 12 and 15% by weight.

The nature of the oily phase of the composition of the invention is not critical and the oily phase can be composed of any fatty substance, in particular oils, conventionally used in the cosmetics field.

Examples of oils which can be used in the composition of the invention, of, for example, oils of vegetable origin (jojoba, avocado, sesame, sunflower, maize, soybean, safflower or grape seed), mineral oils (liquid petrolatum, optionally hydrogenated isoparaffins), synthetic oils (isopropyl myristate, cetearyl octanoate, polyisobutylene, ethylhexyl palmitate or alkyl benzoates), volatile or non-volatile silicone oils, such as polydimethylsiloxanes (PDMS) and cyclodimethylsiloxanes or cyclomethicones, in particular cyclohexadimethylsiloxane and cyclopentadiemthylsiloxane, and fluorinated or fluorosilicone oils. The other fatty substances capable of being present in the oily phase can be, for example, fatty acids, fatty alcohols, such as stearyl alcohol, cetyl alcohol and cetearyl alcohol, and waxes.

The composition of the invention can be provided in the form of an anhydrous product or, by adding at least one aqueous phase, in the form of an oil-in-water (O/W) or water-in-oil (W/O) emulsion or of a multiple emulsion. The term "emulsion" refers to both the emulsifier-free dispersions and dispersions comprising emulsifiers or alternatively dispersions stabilized by solid particles or by lipid spherules of ionic or nonionic type. It is preferable to have an O/W emulsion for use on greasy skin.

When the composition according to the invention is anhydrous, the oily phase is generally present in a concentration ranging from 60 to 99.9% and preferably from 80 to 99.9% of the total weight of the composition. These ranges include all specific values and subranges therebetween, such as 65, 70, 75, 85, 90 and 95% of the total weight of the composition.

In the compositions of the invention in the emulsion form, the aqueous phase of the composition can be present in a concentration ranging, for example, from 5 to 80% and preferably 30 to 70% by weight with respect to the total weight of the composition and the oily phase can be present in a concentration ranging from 5 to 70% and preferably from 10 to 50% by weight with respect to the total weight of the composition.

The emulsions can comprise at least one emulsifier chosen from amphoteric, anionic, cationic or nonionic emulsifiers, used alone or as a mixture.

The emulsifiers are chosen in an appropriate way according to the emulsion to be obtained (W/O or O/W).

For O/W emulsions examples of emulsifiers include:
 as amphoteric emulsifiers, N-acylamino acids, such as N-alkylaminoacetates and disodium cocoamphodiacetate, and amine oxides, such as stearamine oxide;
 as anionic emulsifiers, acylglutamates, such as Disodium hydrogenated tallow glutamate (Amisoft HS-21®, sold by Ajinomoto); carboxylic acids and their salts, such as sodium stearate; phosphoric esters and their salts, such as DEA oleth-10 phosphate; or sulphosuccinates, such as Disodium PEG-5 citrate lauryl sulphosuccinate and Disodium ricinoleamido MEA sulphosuccinate;
 as cationic emulsifiers, alkylimidazolidiniums, such as isostearyl ethylimidonium ethosulphate; or ammonium salts, such as N,N,N-trimethyl-1-docosanaminium chloride (Behentrimonium chloride);
 as nonionic emulsifiers, sugar esters and ethers, such as sucrose stearate, sucrose cocoate and the mixture of sorbitan stearate and sucrose cocoate sold by ICI under the name Arlatone 2121®; polyol esters, in particular of glycerol or of sorbitol, such as glyceryl stearate, polyglyceryl-2 stearate or sorbitan stearate; glycerol ethers; oxyethylenated and/or oxypropylenated ethers, such as the oxyethylenated and oxypropylenated ether of lauryl alcohol comprising 25 oxyethylene groups and 25 oxypropylene groups (CTFA name: PPG-25-laureth-25) and the oxyethylenated ether of the mixture of $C_{12}$–$C_{15}$ fatty alcohols comprising 7 oxyethylene groups (CTFA name: C12–15 Pareth-7); or ethylene glycol polymers, such as PEG-100.

For W/O emulsions, examples of emulsifiers include polyol fatty esters, in particular glycerol or sorbitol fatty esters and in particular polyol isostearic, oleic and ricinoleic esters, such as the mixture of petrolatum, polyglyceryl-3-oleate, glyceryl isostearate, hydrogenated castor oil and ozokerite sold under the name Protegin W® by Goldschmidt, sorbitan isostearate, polyglyceryl diisostearate or polyglyceryl-2 sesquiisostearate; all the sugar esters and ethers, such as methyl glucose dioleate; fatty acid salts, such as magnesium lanolate; or dimethicone copolyols and alkyl dimethicone copolyols, such as lauryl methicone copolyol, sold under the name Dow Corning 5200 Formulation Aid by Dow Corning, and cetyl dimethicone copolyol, sold under the name Abil EM 90® by Goldschmidt.

The emulsifiers can be introduced as is or in the form of a mixture with other emulsifiers and/or with other compounds, such as fatty alcohols or oils.

The composition of the invention can additionally comprise conventional adjuvants, such as water-soluble or fat-soluble dyes, pigments, fragrances, preservatives, sunscreens, sequestering agents (EDTA), fat-soluble or water-soluble active agents, moisturizers, such as polyols and in particular glycerol, or pH adjusters (acids or bases). These adjuvants are used in the proportions usual in the cosmetics field, for example from 0.01 to 20% by weight with respect to the total weight of the composition. This range include all specific values and subranges therebetween, such as 0.02, 0.05, 0.1, 0.2, 0.5, 1, 2, 5, 10, 12 and 15% by weight. These adjuvants and their concentrations are such that they do not modify the property desired for the composition.

Examples of active agents of the active principles of use in treating greasy skin, such as zinc salts, in particular zinc gluconate; antibacterials, such as salicylic acid, triclosan, lipacid, clove extract, octopirox or hexamidine; or antiacne active principles, such as retinoic acid.

The composition of the invention can additionally comprise fillers for the purpose of modifying the texture of the composition. Mention may be made, as fillers which can be used in the composition of the invention, of, for example, in addition to pigments, silica powder; talc; polyamide particles and in particular those sold under the name Orgasol by Atochem; polyethylene powders; microspheres based on acrylic copolymers, such as those made of ethylene glycol dimethacrylate/lauryl methacrylate copolymer which are sold by Dow Corning under the name Polytrap; expanded powders, such as hollow microspheres, in particular the microspheres sold under the name Expancel by Kemanord Plast or under the name Micropearl F 80 ED by Matsumoto; powders formed of natural organic materials, such as maize, wheat or rice starches, which may or may not be crosslinked, such as the powders formed of starch which is crosslinked with octenylsuccinic anhydride which are sold under the name Dry-Flow by National Starch; silicone resin microbeads, such as those sold under the name Tospearl by Toshiba Silicone; and their mixtures. These fillers can be present in amounts ranging from 0 to 40% by weight and preferably from 1 to 10% by weight with respect to the total weight of the composition. These ranges include all specific values and subranges therebetween, such as 2, 5, 12, 15, 20, 30 and 35% by weight.

Although the particles used in the composition of the invention have a better mattifying effect than that of conventional fillers, it is possible, if it is desired to obtain a high covering effect, to have a total amount of fillers and of resin particles in the composition of the invention such that the amount is equal to or greater than the concentration by volume $C^*$. The concentration by volume $C^*$ depends on the oil uptake of the fillers, this oil uptake being measured by determining the volume Vo of the nonvolatile fraction of the oily phase just necessary to fill in the interstices between the particles constituting the fillers. The oil uptake can be measured, for example, according to United States Standard ASTM D281-84, incorporated herein by reference.

If V is the total volume of the fillers and V1 is the volume of the nonvolatile fraction of the oily phase used in the composition, the concentration $C^*$ in % is equal to:

$$\frac{V}{V + Vo} \times 100$$

and the concentration by volume C of the fillers in the composition under consideration is equal to:

$$\frac{V}{V + V1} \times 100$$

The parameters V and V1 can thus be chosen such that C is at least equal to $C^*$.

Furthermore, according to the fluidity of the composition which it is desired to obtain, it is possible to add thereto one or more hydrophilic or lipophilic gelling agents chosen, for example, from clays, polysaccharide gums and their derivatives (xanthan gum, carboxymethylcellulose or hydroxypropylguar), carboxyvinyl polymers or carbomers, polyacrylamides, such as that sold under the name Sepigel 305 by Seppic, and at least partially crosslinked polymers of acrylamidomethylpropanesulphonic acid, such as the product sold under the name Hostacerin AMPS by Hoechst. These gelling agents are generally used at concentrations ranging from 0.1 to 10%, preferably 0.1 to 5% and better still from 0.1 to 3% of the total weight of the composition. These ranges include all specific values and subranges therebetween, such as 0.2, 0.5, 1, 2 and 8% by weight.

The composition of the invention is intended for a topical application and appropriately comprises a physiologically acceptable medium. It finds an application in particular in a large number of cosmetic treatments of the skin, in particular for the purpose of softening imperfections of the relief of the skin, in particular of concealing microrelief features, wrinkles and fine lines, or pores. Due to its mattifying properties, it is also particularly appropriate for treating greasy skin.

Another subject-matter of the invention consequently consists of the cosmetic use of the composition as defined above for softening imperfections of the relief of the skin and/or for concealing microrelief features, wrinkles, fine lines and/or pores of the skin.

The invention also relates to a process for the cosmetic treatment of the skin intended to contribute a matt appearance to it and/or to conceal defects of the relief of the skin, characterized in that a composition as defined above is applied to the skin.

A further subject-matter of the invention is the use of the composition as defined above in the preparation of a composition intended for treating greasy skin.

EXAMPLES

Having generally described this invention, a further understanding can be obtained by reference to certain specific examples which are provided herein for purposes of illustration only and are not intended to be limiting unless otherwise specified. The amounts are given therein as % by weight, except when otherwise mentioned.

Example 1

| Oil-in-Water Emulsion | |
|---|---|
| Oily phase: | |
| Stearyl alcohol | 1% |
| Mixture of glyceryl stearate and PEG-100 (Arlacel 165 from the company ICI Surfactants) | 2% |
| Cyclohexadimethylsiloxane | 10% |
| Aqueous phase: | |
| Urea-formaldehyde resin (Pergopak M3) | 8% |
| Glycerol | |
| Carbomer | 0.2% |
| Xanthan gum | 0.2% |
| Sodium hydroxide | 0.01% |
| EDTA | 0.05% |
| Preservatives | 0.2% |
| Water | q.s. for 100% |

Procedure: The oily phase and the aqueous phase, without the resin, are heated to 80° C., the oily phase is then introduced into the aqueous phase, with stirring, and the resin is subsequently incorporated.

A mattifying composition is obtained which is able to hide wrinkles in a natural way.

Example 2

| Oil-in-Water Emulsion | |
|---|---|
| Oily phase: | |
| Stearyl alcohol | 1% |
| Dimyristyl tartrate/cetearyl alcohol/C12–C15 Pareth-7/PPG-25-Laureth-25 mixture (Cosmacol PSE from the company Enichem) | 1.5% |
| Cyclohexadimethylsiloxane | 10% |
| Aqueous phase: | |
| Melamine-formaldehyde resin (Chrysogyplast PL 100-R) | |
| Glycerol | |
| Carbomer | 0.2% |
| Xanthan gum | 0.2% |

| Oil-in-Water Emulsion | |
|---|---|
| Sodium hydroxide | 0.01% |
| EDTA (sequestering agent) | 0.05% |
| Preservatives | 0.2% |
| Aluminium starch octenylsuccinate (Dry-Flo from the company National Starch) | |
| Water | q.s. for 100% |

Procedure: The oily phase and the aqueous phase, without the resin or the Dry Flo, are heated to 80° C., the oily phase is then introduced into the aqueous phase, with stirring, and the resin and the Dry-Flo are subsequently incorporated.

A composition is obtained which is able to mattify the skin, removing the initial shininess.

Example 3

| Oil-in-Water Emulsion | |
|---|---|
| Oily phase: | |
| Stearyl alcohol | 1% |
| Mixture of glyceryl stearate and PEG-100 (Arlacel 165 from the company ICI Surfactarits) | 2% |
| Cyclohexadimethylsiloxane | 10% |
| Aqueous phase: | |
| Melamine-formaldehyde resin (Chrysogyplast PL 100-R) | 2% |
| Glycerol | 5% |
| Carbomer | 0.2% |
| Xanthan gum | 0.2% |
| Sodium hydroxide | 0.01% |
| EDTA (sequestering agent) | 0.05% |
| Preservatives | 0.2% |
| Aluminium starch octenylsuccinate (Dry-Flo from the company National Starch) | |
| Water | q.s. for 100% |

The procedure is the same as that of Example 2.

A mattifying composition is obtained which is able to remove the shininess of the skin.

Comparative Example

| Oily phase: | |
|---|---|
| Stearyl alcohol | 1% |
| Mixture of glyceryl stearate and PEG-100 (Arlacel 165 from the company ICI Surfactants) | 2% |
| Cyclohexadimethylsiloxane | 10% |
| Aqueous phase: | |
| Silica (Silica beads) | 4% |
| Glycerol | 5% |
| Carbomer | 0.2% |
| Xanthan gum | 0.2% |
| Sodium hydroxide | 0.01% |
| EDTA | 0.05% |
| Preservatives | 0.2% |
| Aluminium starch octenylsuccinate (Dry-Flo from the company National Starch) | 3% |
| Water | q.s. for 100% |

Mattness test: The mattness obtained was measured for the compositions of Example 3, comprising 2% of resin used according to the invention, and of the Comparative Example, comprising 4% of silica. The measurement was made in the following way: The composition was spread over a rubber substrate at the rate of 2 g/cm$^2$, it was allowed to dry and then the reflection was measured using a gonioreflectometer, the result obtained being the ratio R of the specular reflection to the diffuse reflection.

| Composition | Example 3 | Comparative Example |
|---|---|---|
| R | 1.39 ± 0.075 | 1.37 ± 0.075 |

These results show that, with a concentration of resin which is half as great, a mattiness result is obtained which is identical to that obtained with 4% of silica.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 9905043, filed on Apr. 21, 1999, and incorporated herein by reference in its entirety.

What is claimed is:

1. A composition comprising, in a physiologically acceptable medium, at least one oily phase and particles of at least one resin selected from the group consisting of melamine-formaldehyde and urea-formaldehyde resins, wherein particles of said urea-formaldehyde resins have a density of 1.41–1.45 g/cm$^3$ and comprise particles having a particle size of 0.1–5.5 microns.

2. The composition of claim 1, wherein the resin particles have a number-average size ranging from 0.1 to 20 µm.

3. The composition of claim 1, wherein the amount of resin particles ranges from 0.05 to 20% by weight with respect to the total weight of the composition.

4. The composition of claim 1, which is anhydrous.

5. The composition of claim 1, wherein the oily phase represents from 60 to 99.9% by weight with respect to the total weight of the composition.

6. The composition of claim 1, which is in the form of an emulsion.

7. The composition of claim 1, which contains an aqueous phase representing from 5 to 80% by weight with respect to the total weight of the composition.

8. The composition of claim 6, wherein the oily phase represents from 5 to 70% by weight with respect to the total weight of the composition.

9. The composition of claim 6, further comprising at least one emulsifier.

10. The composition of claim 1, further comprising one or more adjuvants selected from the group consisting of dyes, pigments, fragrances, preservatives, sunscreens, fat-soluble or water-soluble active agents, sequestering agents, moisturizers, gelling agents and fillers.

11. The composition of claim 10, wherein fillers are selected from the group consisting of silica powder, talc, polyamide particles, polyethylene powders, microspheres comprising acrylic copolymers, expanded powders, powders formed of natural organic materials, silicone resin microbeads, and mixtures thereof.

12. The composition of claim 1, comprising a total amount of fillers and of resin particles equal to or greater than the concentration by volume C*, wherein C* is defined as $$\frac{V}{V+V_o} \times 100$$

wherein V is the total volume of fillers and Vo is the volume of the non-volatile fraction of the oily phase just necessary to fill in the interstices between the particles constituting the fillers.

13. A method of cosmetically treating skin, comprising applying the composition of claim 1 to the skin.

14. A method of softening skin defects, comprising applying the composition of claim 1 to the skin.

15. A method of producing a matt appearance on skin, comprising applying the composition of claim 1 to the skin.

16. A method of concealing defects of the relief of the skin, comprising applying the composition of claim 1 to the skin.

17. A method of treating greasy skin, comprising applying the composition of claim 1 to greasy skin.

18. A method of preparing the composition of claim 1, comprising combining the oily phase, resin particles and physiologically acceptable medium.

19. The composition of claim 1, wherein the resin is a melamine-formaldehyde resin.

20. The composition of claim 19, wherein the melamine-formaldehyde resin has a number-average particle size of approximately 0.1 to 0.5 $\mu$m.

21. The composition of claim 1, wherein the resin is a urea-formaldehyde resin.

22. A composition comprising, in a physiologically acceptable medium, at least one oily phase and particles of at least one urea-formaldehyde resin, wherein the urea-formaldehyde resin has a number-average particle size of approximately 5 to 20 $\mu$m.

23. The composition of claim 3, wherein the amount of resin particles ranges from 0.1 to 10% by weight with respect to the total weight of the composition.

* * * * *